United States Patent
Eades (10) Patent No.: US 11,160,891 B2
(45) Date of Patent: Nov. 2, 2021

(54) METHODS AND APPARATUS FOR LOW-PRESSURE RADIANT ENERGY PROCESSING OF CANNABIS

(71) Applicant: Tilray, Inc., Seattle, WA (US)

(72) Inventor: Caleb Joshua Eades, Nanaimo (CA)

(73) Assignee: Tilray, Inc., Nanaimo (CA)

( * ) Notice: Subject to any disclaimer, the term of this patent is extended or adjusted under 35 U.S.C. 154(b) by 0 days.

(21) Appl. No.: 15/892,385

(22) Filed: Feb. 8, 2018

(65) Prior Publication Data

US 2018/0221522 A1 Aug. 9, 2018

Related U.S. Application Data

(60) Provisional application No. 62/456,480, filed on Feb. 8, 2017.

(51) Int. Cl.
- *A61L 2/12* (2006.01)
- *A61L 2/02* (2006.01)
- *A61L 2/08* (2006.01)
- *A61L 2/00* (2006.01)

(52) U.S. Cl.
CPC .................. *A61L 2/12* (2013.01); *A61L 2/00* (2013.01); *A61L 2/02* (2013.01); *A61L 2/08* (2013.01); *A61L 2202/14* (2013.01); *A61L 2202/21* (2013.01)

(58) Field of Classification Search
CPC ..... A61L 2/12; A61L 2/00; A61L 2/08; A61L 2/02; A61L 2202/21; A61L 2202/14
See application file for complete search history.

(56) References Cited

U.S. PATENT DOCUMENTS

| | | | |
|---|---|---|---|
| 5,122,633 A * | 6/1992 | Moshammer | A61L 2/07 219/686 |
| 5,458,897 A | 10/1995 | Pare | |
| 5,939,116 A * | 8/1999 | Ono | A23L 3/0055 426/242 |
| 8,240,213 B2 | 8/2012 | Donaty | |
| 8,445,034 B1 | 5/2013 | Coles, Jr. | |
| 10,517,308 B2 * | 12/2019 | Rehkopf | A23B 7/012 |
| 2010/0062121 A1 | 3/2010 | Farid et al. | |

(Continued)

FOREIGN PATENT DOCUMENTS

| WO | WO2015054163 A1 | 4/2015 |
| WO | WO2015058027 A1 | 4/2015 |
| WO | WO 19041017 A1 | 3/2019 |

OTHER PUBLICATIONS

Hazekamp, Evaluating the Effects of Gamma-Irradiation for Decontamination of Medicinal Cannabis (Year: 2016).*

(Continued)

*Primary Examiner* — Sean E Conley
*Assistant Examiner* — Brendan A Hensel
(74) *Attorney, Agent, or Firm* — Kelley Drye & Warren LLP (57) ABSTRACT

Methods and apparatuses for reducing the bioburden of cannabis using low-pressure radiant energy processing. The present invention achieves sufficient microbial killing and/or adequate drying without impacting product quality (terpene loss, smell, color, texture, etc.) by appropriate determination and application of pressure(s) and radiant energy (e.g., microwave intensity).

20 Claims, 3 Drawing Sheets

(56) References Cited

U.S. PATENT DOCUMENTS

2014/0141105 A1    5/2014  Pritchett
2015/0096189 A1    4/2015  Hawes et al.

OTHER PUBLICATIONS

Bogart, "Moisture Content vs. Water Activity: Use Both to Optimize Food Safety and Quality", Apr. 1, 2015, Kett Science of Sensing, pp. 1-6.
Vian et al., "Microwave hydrodiffusion and gravity, a new technique for extraction of essential oils," Mar. 2, 2008, Journal of Chromatography A, pp. 14-17.
Patent Cooperation Treaty Application PCT/US2018/17451 International Search Report and Written Opinion of the International Searching Authority, dated Apr. 23, 2018.
"Microwave-Assisted Drying of Biomaterials", V. Orsat, W. Yang, V. Changrue and G.S. V. Ragahvan, Sep. 1, 2007.
"Characteristics of Hemp (*Cannibis stavia* L.) Seed Oil", B. Dave Oomah, Muriel Busson, David V. Godrey, John C.G. Drover, Jan. 1, 2014.
"Combined Microwave Vacuum Drying", Christine H. Seaman, Timothy D. Durance, Liana Drummond, Da-Wen Sun.
Office Action issued by Colombia Patent Office for Patent Application No. NC2019/0008594 dated May 13, 2021.
European Search Report Issued for European Patent Application No. 18751203.3 dated Nov. 26, 2020.

\* cited by examiner

METHODS AND APPARATUS FOR LOW-PRESSURE RADIANT ENERGY PROCESSING OF CANNABIS

This application may contain material that is subject to copyright, mask work, and/or other intellectual property protection. The owner of such intellectual property has no objection to the facsimile reproduction of the disclosure by anyone as it appears in published Patent Office file/records, but otherwise reserves all rights.

FIELD OF THE INVENTION

This invention relates to the field of cannabis processing and, more particularly, to methods that may be used to reduce the bioburden of cannabis.

BACKGROUND OF THE INVENTION

Traditional methods for reducing the bioburden of cannabis (e.g., killing microbes on the product) include gamma irradiation and electron irradiation. Such methods can cause elevated temperatures and/or differential pressures that can damage a cannabis product by, for example, causing loss of important compounds such as terpenes, causing discoloration, and/or changing the smell of the final product.

There is therefore a need for improved methods of reducing the bioburden of cannabis that overcome some or all of the drawbacks of traditional methods.

SUMMARY OF THE INVENTION

The present invention is directed to novel methods and apparatuses for reducing the bioburden of cannabis, including novel methods and apparatuses for low pressure radiant energy processing of cannabis. The present invention achieves sufficient microbial killing and/or adequate drying without impacting product quality (terpene loss, smell, color, texture, etc.) by appropriate determination and application of pressure(s) and radiant energy (e.g., microwave intensity).

It is an object of the present invention to minimize loss of important volatile compounds from cannabis during processing, such as cannabinoids and/or terpenes, and to maintain the color, appearance, smell, and/or texture of the end product (i.e., processed cannabis).

It is also an object of the present invention to allow a significant reduction in the drying time, as compared to air drying or other known drying techniques.

It is also an object of the present invention to provide new, rapid processing of cannabis from harvest to various points of downstream manufacturing, with overall processing times significantly reduced from typical processing times. The overall manufacturing of cannabis from harvest to packaging may be accomplished in a single day, and may include: harvest, bucking, drying, bioburden reduction, trimming, and packaging.

Numerous variations may be practiced in the preferred embodiment.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the disclosed subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

The invention may be understood more readily by reference to the following detailed descriptions of preferred embodiments of the invention. However, techniques, systems, and operating structures in accordance with the invention may be embodied in a wide variety of forms and modes, some of which may be quite different from those in the disclosed embodiments. Consequently, the specific structural and functional details disclosed herein are merely representative, yet in that regard, they are deemed to afford the best embodiment for purposes of disclosure and to provide a basis for the claims herein, which define the scope of the invention.

The disclosed methods and apparatuses provide significant advantages over existing techniques for bioburden reduction. According to some embodiments, processing can include drying and/or bioburden reduction, either as separate or combined processes.

Figure 1A:
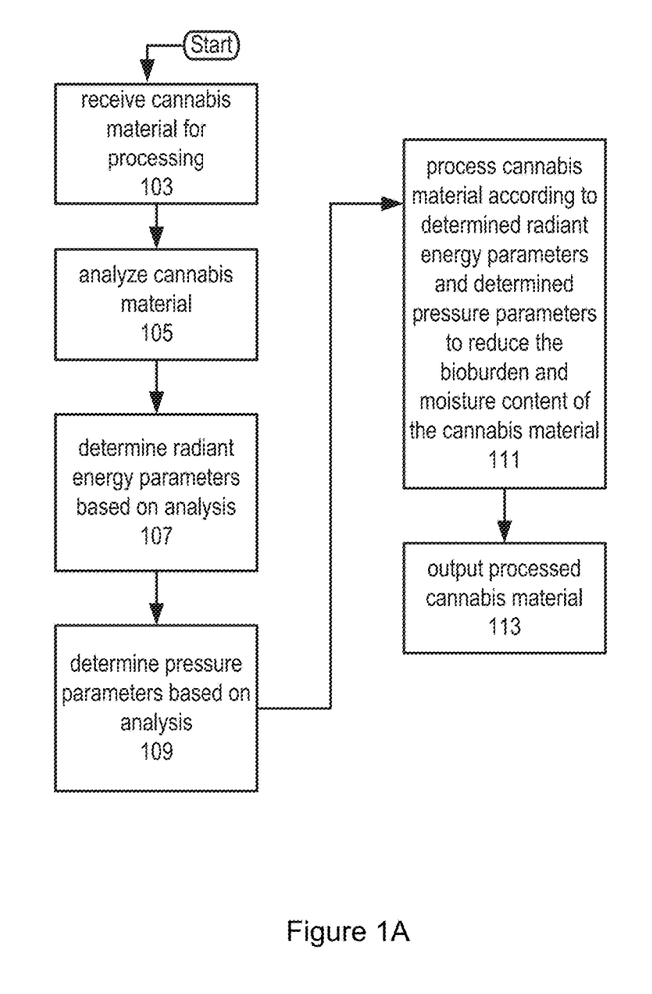
FIG. 1A is a flow diagram illustrating an example of cannabis processing according to the present invention.

As illustrated in the example flow diagram in FIG. 1A, according to some embodiments of the disclosure, a method for low-pressure, radiant energy cannabis processing can comprise receiving cannabis material for processing 103. The cannabis material received at step 103 may be unprocessed or partially processed.

The received cannabis material (e.g., leaf, flower, and/or stem) can be placed into a container and/or onto a transporter (e.g., conveyor belt). Then, the cannabis material is analyzed 105. The analysis can be one or more of a number of analyses (macroscopic and microscopic, chemical, safety, etc.), including, by way of non-limiting example, visual/photographic/video analysis, laser analysis, spectral/spectrometer analysis, near infrared spectroscopy (NIR), moisture analysis, analysis of components (e.g., THC, CBD, terpenoids, flavonoids, etc.), bioburden analysis (e.g., fungus/mycotoxin, mold, mildew, microbes, bacteria, etc.), enzyme-linked immunoadsorbent assay (ELISA), gas chromatography (GC), high performance liquid chromatography (HPLC), thin layer chromatography (TLC), nuclear magnetic resonance (NMR), quantitative Polymerase Chain-Reaction (qPCR), pesticide residue analysis, etc. Then, based on the analysis/analyses, radiant energy parameters 107 and/or pressure parameters 109 for the cannabis material are determined/calculated such that the bioburden and humidity/moisture content are reduced to or below specified levels.

The cannabis material is then processed 111 with radiant energy according to the determined radiant energy parameters and/or pressure according to the pressure parameters such that the bioburden of the cannabis material is eliminated or reduced to at or below a specified threshold, and/or the moisture content of the cannabis material is reduced to at or below a specified threshold, while maintaining a terpene (and/or other cannabis component) content of the cannabis material at or above a specified threshold.

Mildew is a common bioburden for cannabis, though also one of the least harmful, typically only imparting an unpleasant taste for most consumers. However, if a consumer has lung impairments, a compromised immune system, or allergies to molds, mildew can be a serious problem. As such, if it is determined that a particular batch of cannabis material has or could have a minor mildew problem, the radiant energy parameters and/or pressure parameters may be configured to kill the mildew and/or dry out the cannabis material. In some embodiments, if the bioburden is determined to be over a specified threshold, the cannabis material may be rejected or marked for alternative processing (e.g., returned to origin, disposed of, or processed for extract in such a way that bioburden is completely eliminated).

Bacteria and fungi have specific water requirements. Many plant-based foods have high moisture content that may support significant microbial replication, thus posing a risk if they are not properly cooked. Rather than focusing on moisture content, methods and apparatus according to the present invention can utilize "water activity" in determining the potential for microbial growth, where water activity is a measure of the available water that can be utilized for microbiological growth. Water activity increases non-linearly with moisture content, and in a particular way that is unique for each material. High-moisture foods with high sugar and/or salt content typically have a low water activity, as the solute concentrations result in a majority of the water being functionally unavailable.

Figure 1B:
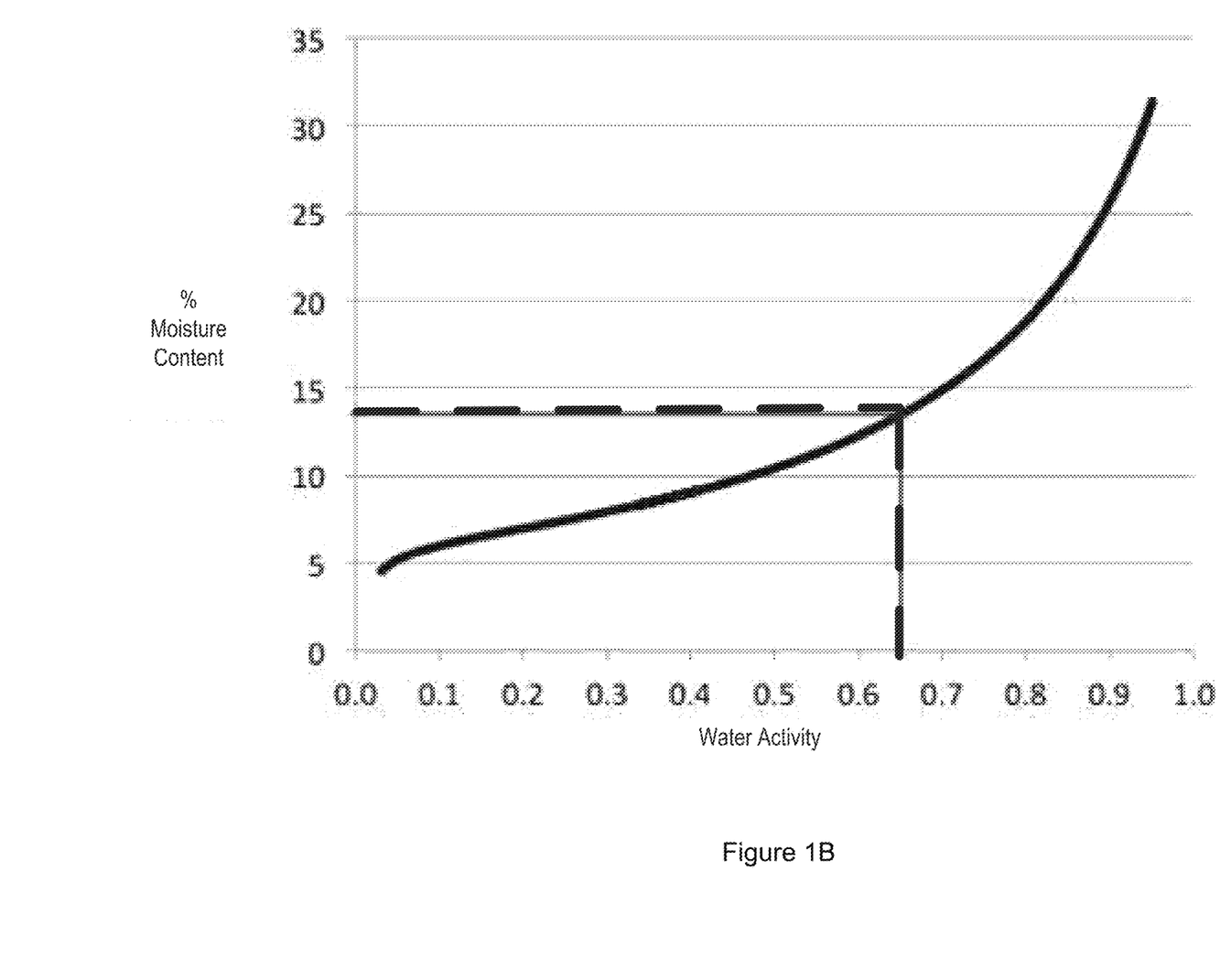
FIG. 1B depicts an example cannabis moisture sorption isotherm.

As discussed herein, water activity ranges from 0 to 1, and while most pathogens cannot grow below a water activity of 0.9, some fungi can grow slowly at water activities as low as 0.611. FIG. 1B illustrates a Cannabis moisture sorption isotherm generated from averages of samples of cannabis flowers. As can be seen, a water activity of 0.65 generally corresponds to a moisture content of 14% (+/−2%).

According to some embodiments, methods according to the present invention are configured to process cannabis material such that the processed cannabis material has a water activity less than 0.60, less than 0.59, less than 0.58, less than 0.57, less than 0.56, less than 0.55, less than 0.54, less than 0.53, less than 0.52, less than 0.51, less than 0.50, less than 0.49, less than 0.48, less than 0.47, less than 0.46, less than 0.45, less than 0.44, less than 0.43, less than 0.42, less than 0.41, less than 0.40, less than 0.39, less than 0.38, less than 0.37, less than 0.36, less than 0.35, less than 0.34, less than 0.33, less than 0.32, less than 0.31, or less than 0.30. According to some embodiments, methods according to the present invention are configured to process cannabis material such that the processed cannabis material has a water activity between about 0.1 and 0.8, between about 0.30 and 0.60, between about 0.35 and 0.55, or between about 0.40 and 0.50. According to some embodiments, methods and apparatus according to the present invention are configured to process cannabis material such that the processed cannabis material has moisture content of between 1% and 15%, between about 2% and about 13%, or between about 5% and about 10%.

In some embodiments according to the present invention, the method can include multiple exposures to radiant energy and/or exposures to radiant energy for a variety of times and/or intensities, and/or at a variety of pressures/reduced pressures relative to atmospheric pressure. Exposure to radiant energy can occur at the same time as a pressure other than atmospheric pressure is applied to the cannabis. In addition or in the alternative, exposure to radiant energy can occur at a different time than when pressure other than atmospheric pressure is applied to the cannabis. Also, the exposure to radiant energy and application of pressure other than atmospheric pressure can occur in the same processing chamber. In the alternative, exposure to radiant energy and application of pressure other than atmospheric pressure can occur in separate processing chambers.

In some embodiments according to the present invention, terpenes and/or other cannabis components may be removed from the cannabis material during the processing, and in some such embodiments, such removed materials can be added back in. For example, if during processing of a given batch, it is determined that a particular terpene is being removed (e.g., via sensors that monitor air flow out of a processing chamber), that terpene can either be recovered (e.g., via extracting/condensing the terpene from air/moisture removed from the cannabis material) and added back to the cannabis material, and/or a replacement terpene can be added to the cannabis material.

Figure 2:
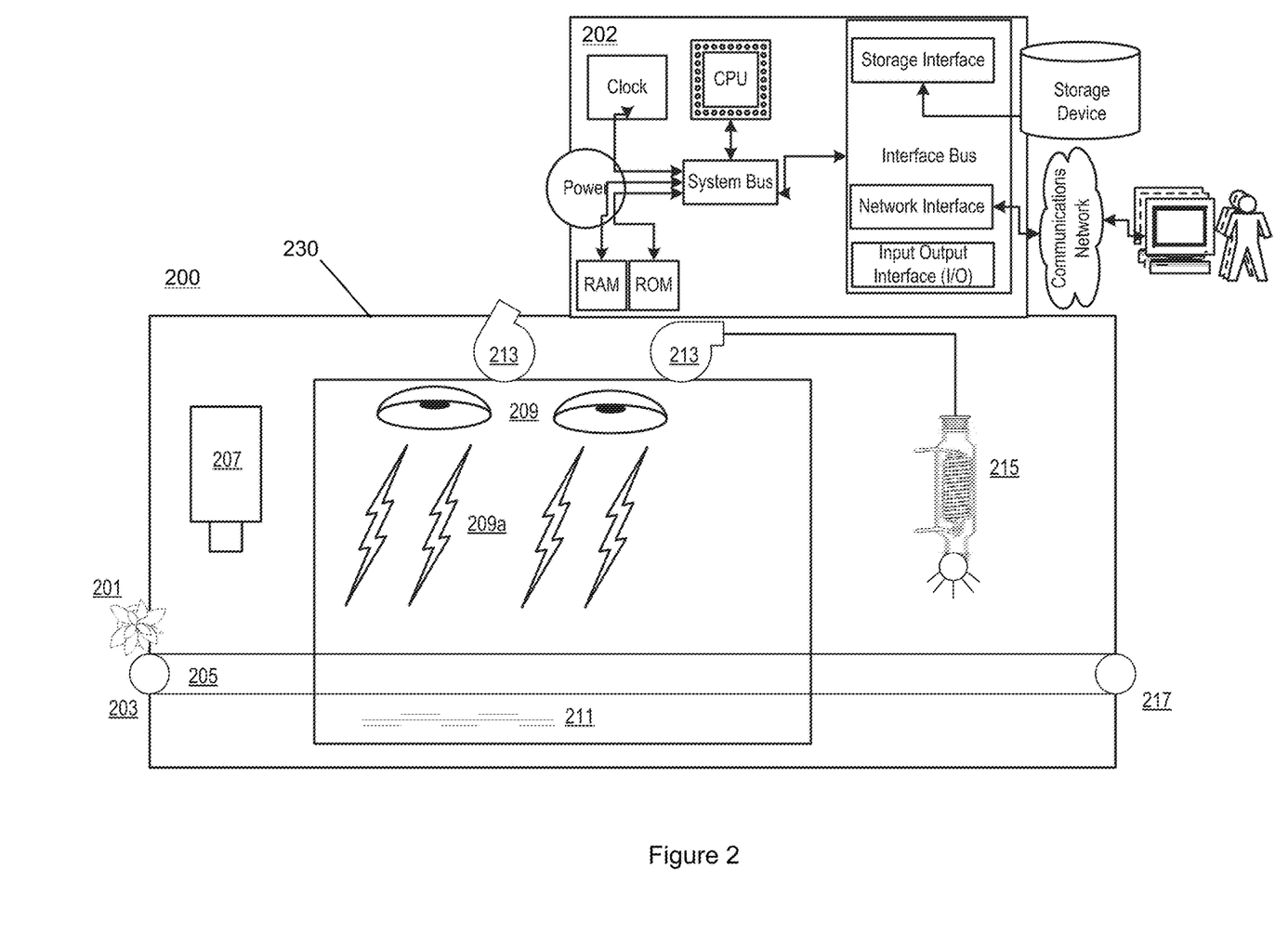
FIG. 2 depicts an example cannabis processing apparatus according to the present invention.

In some embodiments according to the present invention, the apparatus and/or method are configured such that the bioburden of the processed cannabis material is one or more of the following:

Total Viable Aerobic Bacteria Count <100,000 CFU
Total Yeast and Mold Count <10,000 CFU
Bile-tolerant Gram-Negative Bacteria <1000 CFU
Total Coliforms Count <1000 CFU
*E. coli* (pathogenic strains)—not detected in one gram
*Salmonella* spp.—not detected in one gram
Gram-Negative bacteria <10,000 CFU
*Aspergillus*—none detected
*Penicillium*—none detected
*Mucor*—none detected
Thermophilic Actinomycetes—none detected Some embodiments of the present invention include low-pressure, radiant energy cannabis process apparatuses. An example overview of an apparatus is illustrated in FIG. 2. Such an apparatus 200 can comprise housing 230 having an intake 203 configured to receive unprocessed or partially processed cannabis material 201. Housing 230 may be any shape or size and may comprise any structure, including a building or a room within a building. Intake 203 may be a door, a chute, a slot, an aperture, or any other structure for receiving cannabis material 201.

Apparatus 200 and/or a subdevice thereof can include a computer, computer processor, control circuit, microcontroller, and/or other computer device 202 configured to process data from one or more sensors, subcomponents, inputs, etc., and control one or more sensors, subcomponents, outputs, etc.

Apparatus 200 can include a transporter 205 (e.g., conveyor, flow path, ramp, chute, rollers) configured to move cannabis material through apparatus 200. Cannabis material 201 can be in a container that is moved, for example on a conveyor. In the alternative, apparatus 200 can move or be moved over the cannabis material 201.

Apparatus 200 can include one or more analyzers 207 configured to analyze cannabis material 201 for one or more of a plurality of aspects, including bioburden, water content, weight, terpene content, color, etc. Analyzer 207 can include a visual/photographic/video analyzer, a laser analyzer, a spectral/spectrometer analyzer, a scale, a near infrared spectroscopy (NIR) device, a moisture analyzer, an enzyme-linked immunoadsorbent assay (ELISA) device, a gas chromatography (GC) device, a temperature sensor, a pressure sensor, a high performance liquid chromatography (HPLC) device, a thin layer chromatography (TLC) device, a nuclear magnetic resonance (NMR) imager, a quantitative Polymerase Chain-Reaction (qPCR) device, etc.

Based on data from the one or more analyzers 207, apparatus 200 can determine (e.g., via computer device 202) radiant energy parameters and pressure parameters for the cannabis material. For example, if analyzer 207 provides data that is processed by computer device 202 to determine the water activity level of cannabis material 201 (e.g., if analyzer 207 is a LOD (loss-on-drying) device, spectroscopy device, electrolytic sensor, piezoelectric sorption device, etc.), computer device 202 may further determine the appropriate radiant energy parameters and pressure parameters to reduce the water activity level of cannabis material 201 to at or below a particular level (e.g., 0.60).

The radiant energy parameters may include radiant energy intensity, exposure time to radiant energy, and/or a plan or schedule for radiant energy exposure (with varying or intermittent radiant energy exposure times and/or intensities). The pressure parameters may include what pressure(s) (e.g., relative to outside/atmospheric pressure) are to be applied to the cannabis material. The pressure parameters may further include cycling at different pressures, a pressure gradient, and/or applying certain pressures at certain radiant energy exposures. In some embodiments according to the present invention, the applied pressure may be less than outside/atmospheric pressure.

Apparatus 200 can include one or more radiant energy emitters 209 configured to emit and/or provide radiant energy 209a to the cannabis material, based on the determined radiant energy parameters. In some embodiments, the one or more radiant energy emitters 209 can be configured to emit non-ionizing radiant energy at a frequency from about 1 GHz to about 8 GHz, and a wavelength from about 30 cm to about 3.75 cm. In some embodiments, at least one radiant energy emitter is configured to emit radiant energy at a frequency of between about 400 MHz and 8000 MHz, including any integers there between, including but not limited to about 433 MHz, 433.92 MHz, about 434 MHz, about 915 MHz, 915 MHz, about 2450 MHz, 2450 MHz, about 5800 MHz, or 5800 MHz. In some embodiments, the one or more radiant energy emitters can include a magnetron/cavity magnetron and/or the like to generate the radiant energy. In some embodiments, the one or more radiant energy emitters and/or the apparatus can include waveguides, fixed and/or movable, that direct and/or redirect the emitted radiant energy, in some implementations, directing radiant energy such that the radiant energy is dispersed in a generally uniform (and/or uniform over time) manner to the cannabis material. In some embodiments, the apparatus can be configured such that radiant energy received by the cannabis material is from about 0.1 kW/kg to about 50 kW/kg, including about 0.2 kW/kg, about 0.3 kW/kg, about 0.4 kW/kg, about 0.5 kW/kg, about 0.6 kW/kg, about 0.7 kW/kg, about 0.8 kW/kg, about 0.9 kW/kg, about 1 kW/kg, about 5 kW/kg, about 10 kW/kg, about 15 kW/kg, about 20 kW/kg, about 25 kW/kg, about 30 kW/kg, about 35 kW/kg, about 40 kW/kg, about 45 kW/kg, about 49 kW/kg, or any integers there between.

In some embodiments, the apparatus can be configured such that cannabis material 201 is exposed to the radiant energy 209a for a single radiant energy session or for a plurality of radiant energy sessions. In some embodiment, apparatus 200 can be configured such that a radiant energy session is less than a second, about 1 second, 5 seconds, 10 seconds, 20 seconds, 30 seconds, 45 seconds, 60 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 45 minutes, 60 minutes, 90 minutes, 120 minutes, 150 minutes, 180 minutes, 240 minutes, 300 minutes, 360 minutes, 420 minutes, 480 minutes, 540 minutes, or any integers there between. In some embodiments, the apparatus can be configured such that the total exposure time of exposure to radiant energy from the apparatus for cannabis material (i.e., the total of the radiant energy sessions) is or about 5 seconds, 10 seconds, 20 seconds, 30 seconds, 45 seconds, 60 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 45 minutes, 60 minutes, 90 minutes, 120 minutes, 150 minutes, 180 minutes, 240 minutes, 300 minutes, 360 minutes, 420 minutes, 480 minutes, 540 minutes, or any integers there between.

Apparatus 200 can include one or more pressure pumps 213 or the like configured to control environmental pressure(s) (i.e., the pressure(s) that cannabis material 201 is exposed to during processing), based on the determined pressure parameters. The pressure(s) can be target pressures and/or set point pressures. The pressures may follow a curve or line as the pressure changes from an initial pressure (e.g., atmospheric or external pressure) to or towards the environmental pressure(s) based on the determined pressure parameters. In some embodiments, apparatus 200 can be configured such that cannabis material 201 is exposed to one or more altered pressures from about 500000 Pascal (Pa) to 1 Pa, including 500000 Pa, 400000 Pa, 300000 Pa, 200000 Pa, 101325 Pa, 100000 Pa, 50000 pa, 10000 Pa, 5000 Pa, 1000 Pa, 500 Pa, 100 Pa, 50 Pa, 10 Pa, 1 Pa, or any integers there between. For example, in one embodiment cannabis material 201 may be exposed to pressure of approximately 20,000 Pa. In another exemplary embodiment, cannabis material 201 may be exposed to pressure of approximately 40,000 Pa.

In some embodiments according to the present invention, apparatus 200 can be configured such that cannabis material 201 is exposed to the environmental pressure(s) for a single pressure session, or for a plurality of pressure sessions. In some embodiment, the apparatus can be configured such that a pressure session is about 1 second (e.g., the target pressure is reached and then continues on to the next pressure or returns to baseline; alternatively, the session can be the time that the pressure is away from a baseline pressure, such that it includes the time to reach the target pressure and/or to return from the target pressure to the baseline or next pressure), about 5 seconds, 10 seconds, 20 seconds, 30 seconds, 45 seconds, 60 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 45 minutes, 60 minutes, 90 minutes, 120 minutes, 150 minutes, 180 minutes, 240 minutes, 300 minutes, 360 minutes, 420 minutes, 480 minutes, 540 minutes, or any integers there between. In some embodiments, apparatus 200 can be configured such that the total time of exposure to altered pressure(s) from the apparatus for cannabis material 201 (i.e., the total of the pressure sessions, or total of sessions at a particular altered pressure) is about 5 seconds, 10 seconds, 20 seconds, 30 seconds, 45 seconds, 60 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 45 minutes, 60 minutes, 90 minutes, 120 minutes, 150 minutes, 180 minutes, 240 minutes, 300 minutes, 360 minutes, 420 minutes, 480 minutes, 540 minutes, or any integers there between.

In some embodiments according to the present invention, apparatus 200 is configured such that one or more pressure sessions corresponds or is related to one or more radiant energy sessions. In some embodiments, the apparatus includes a temperature controller 211, such as a heater or cooler, configured to alter the temperature of the environment in the apparatus and/or the temperature of the cannabis material. For example, in some embodiments, temperature controller 211 is configured to raise, lower, or maintain the temperature of cannabis material 201, such that cannabis material 201 reaches, exceeds, does not exceed, stays below, or does not go below a given temperature during a specified time period (e.g., during a given pressure session and/or radiant energy session, or across one or more sessions). For example, the apparatus can be configured such that the temperature of the cannabis material does not exceed a given temperature for more than a specified time (e.g., does not exceed 50 C for more than 1 minute, or does not exceed 60 C for the full time the cannabis material spends in the apparatus). In some embodiments, a given temperature is between about 80 C and about −120 C, including 80 C, 70 C, 60 C, 50 C, 40 C, 30 C, 20 C, 10 C, 5 C, 0 C, −5 C, −10 C, −20 C, −30 C, −40 C, −50 C, −60 C, −70 C, −80 C, −90 C, −100 C, −110 C, −120 C, or any integers there between. In some embodiments, temperature controller 211 can work with/integrate with components of apparatus 200, e.g., sensors, transporter 205, pressure pump(s) 213 and/or radiant energy emitters 209, such that temperature is controlled dynamically based on or within specified and/or determined parameters.

Apparatus 200 can include an outlet or output 217 configured to dispense processed cannabis material 201. In some embodiments, the cannabis has a reduced bioburden compared with unprocessed cannabis material. In some embodiments, the cannabis has a reduced bioburden compared with air-dried cannabis material. According to some embodiments, apparatus 200 is configured to process cannabis material such that the processed cannabis material has a water activity less than 0.80, less than 0.75, less than 0.70, less than 0.65, less than 0.60, less than 0.59, less than 0.58, less than 0.57, less than 0.56, less than 0.55, less than 0.54, less than 0.53, less than 0.52, less than 0.51, less than 0.50, less than 0.49, less than 0.48, less than 0.47, less than 0.46, less than 0.45, less than 0.44, less than 0.43, less than 0.42, less than 0.41, less than 0.40, less than 0.39, less than 0.38, less than 0.37, less than 0.36, less than 0.35, less than 0.34, less than 0.33, less than 0.32, less than 0.31, or less than 0.30. According to some embodiments, apparatus 200 is configured to process cannabis material such that the processed cannabis material has a water activity between about 0.1 and 0.8, between about 0.30 and 0.60, between about 0.35 and 0.55, or between about 0.40 and 0.50.

In some embodiments according to the present invention, apparatus 200 may be configured to maintain the terpene level and/or level of one or more components of cannabis material 201 above a given threshold, such as at a percentage relative to the level prior to processing of cannabis material 201, or as a percentage relative to cannabis material that has been air-dried. For example, in some embodiments, the terpene content (for one or more terpenes) of the cannabis material can be greater than 50% of baseline, greater than 60% of baseline, greater than 70% of baseline, greater than 75% of baseline, greater than 76% of baseline, greater than 77% of baseline, greater than 78% of baseline, greater than 79% of baseline, greater than 80% of baseline, greater than 81% of baseline, greater than 82% of baseline, greater than 83% of baseline, greater than 84% of baseline, greater than 85% of baseline, greater than 86% of baseline, greater than 87% of baseline, greater than 88% of baseline, greater than 89% of baseline, greater than 90% of baseline, greater than 91% of baseline, greater than 92% of baseline, greater than 93% of baseline, greater than 94% of baseline, greater than 95% of baseline, greater than 96% of baseline, greater than 97% of baseline, greater than 98% of baseline, or greater than 99% of baseline, where the baseline is based on air-dried cannabis material, or based on cannabis material 201 prior to processing.

In some embodiment according to the present invention, apparatus 200 is configured to operate the various components within parameters and/or dynamically such that the terpene(s) and/or other cannabis components of cannabis material 201 are maintained while still reducing the bioburden and/or reaching a specified water activity level.

In some embodiments according to the present invention, apparatus 200 is configured to remove a portion of one or more terpenes (and/or other cannabis components) present in cannabis material 201, e.g., via the pumping and radiant energy exposure, and add removed terpene(s)/cannabis component(s) back to cannabis material 201 via an addition device 215, such as a terpene dispenser configured to add one or more terpenes to cannabis material 201.

In some embodiments according to the present invention, the one or more terpenes added to cannabis material 201 include one or more terpenes removed from cannabis material 201. In some embodiments, the added terpenes or the like can be retrieved and/or condensed from the outflow from pressure pump(s) 213 by an extractor (not shown), or alternatively, can be added from a stock source.

Apparatus 200 may have separate areas, chambers, compartments, rooms, portions, or other separate spaces in which one or more of the components described above may be located. For example, analyzer 207 may be located in the same portion of apparatus 200 as radiant energy emitters 209, or in a different portion. As another example, pressure pumps 213 may be located in the same area of apparatus 200 as radiant energy emitters 209, or a different area. If one or more components are separated in different areas of apparatus 200, transporter 205 may transport cannabis material 201 to and between each area.

For bioburden reduction/microbial killing, sufficient radiant energy and pressure (e.g., reduced/vacuum pressure) may be applied to cause the temperature of cannabis material 201 to elevate to a sufficient level to effectively kill microbes. The temperature level and duration may be altered depending on the moisture content of cannabis material 201. Cannabis material 201 that has more moisture may require shorter exposure times, since the high specific heat capacity of water can accelerate microbial killing and allow sufficient log-reduction in a short period of time. Thus, it can be advantageous, in some embodiments, to modulate the processing parameters to cause temperature elevation early in the cycle while the cannabis material 201 is still wet, which can cause more effective microbial killing in a shorter period of time than on drier product. Such implementations can also minimize damage to cannabis material 201, since wetter product is less susceptible to discoloration, change in smell, and other damage associated with elevated temperatures.

According to some embodiments, for the drying process, excessive low pressure can cause undesirable loss of terpenes, and heating of cannabis material 201 later in the cycle can cause terpene loss, and may also cause visual damage and impact the smell of cannabis material 201. Thus some embodiments are configured such that heating later in the treatment and/or drying cycle is reduced relative to earlier in the cycle.

Alternatively or additionally, in some embodiments, the configuration of cannabis material 201 in apparatus 200, for instance density of cannabis material 201, can be altered to achieve optimal drying. In some embodiments, more aggressive parameters/conditions such as radiant energy (e.g., microwave) intensity and/or pressure/vacuum can be used early in the cycle to accelerate the drying and/or killing process, and then gentler (i.e., lower/less intense) conditions may be used later in the cycle to mitigate product quality issues. Thus, in some such embodiments, the overall cycle time may be somewhat longer than a cycle with a single set of parameters. In some embodiments, the treatment cycle may include multiple phases with different parameters, in order to optimize the desired effects without causing product quality issues.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, some embodiments may be implemented using hardware, software, and/or a combination thereof. When implemented in software, the software code can be executed on any suitable processor or collection of processors, whether provided in a single computer or distributed among multiple computers.

Further, it should be appreciated that computer device 202 may be embodied in any of a number of forms, such as a rack-mounted computer, a desktop computer, a laptop computer, or a tablet computer. Additionally, computer device 202 may be embedded in a device not generally regarded as a computer but with suitable processing capabilities, including a Personal Digital Assistant (PDA), a smart phone or any other suitable portable or fixed electronic device. Also, computer device 202 may have one or more input and output devices, including one or more displays. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, computer device 202 may receive input information through speech recognition or in other audible format.

Computer device 202 and one or more other computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks. The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. In this respect, various disclosed concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure. Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

A flow diagram is used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedia components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. A method for processing cannabis, comprising:
   receiving cannabis material;
   performing an analysis of the cannabis material, wherein the type of analysis is selected from the group consisting of photographic/video analysis, laser analysis, spectral/spectrometer analysis, near infrared spectroscopy (NIR), moisture analysis, analysis of components, bioburden analysis, enzyme-linked immunoadsorbent assay (ELISA), gas chromatography (GC), high performance liquid chromatography (HPLC), thin layer chromatography (TLC), nuclear magnetic resonance (NMR), quantitative Polymerase Chain-Reaction (qPCR), and pesticide residue analysis;
   determining, based on the analysis, a first radiant energy level;
   determining, based on the analysis, a first pressure level; and
   processing the cannabis material with radiant energy according to the first radiant energy level and with pressure according to the first pressure level;
   wherein the first radiant energy level and the first pressure level are determined so as to reduce a bioburden of the cannabis material to below a predetermined threshold, reduce the moisture content of the cannabis material to below a predetermined threshold, and maintain a terpene content of the cannabis material above a predetermined threshold.

2. The method of claim 1 wherein the first radiant energy level is 7 kilowatts.

3. The method of claim 2 wherein the first pressure level is approximately 40,000 Pascal.

4. The method of claim 3 wherein the cannabis material is processed for 10 minutes with radiant energy according to the first radiant energy level and with pressure according to the first pressure level.

5. The method of claim 1 wherein the first pressure level is approximately 40,000 Pascal.

6. The method of claim 5 wherein the cannabis material is processed for 10 minutes with radiant energy according to the first radiant energy level and with pressure according to the first pressure level.

7. The method of claim 1 wherein the first radiant energy level is 5 kilowatts.

8. The method of claim 7 wherein the first pressure level is approximately 20,000 Pascal.

9. The method of claim 8 wherein the cannabis material is processed for 15 minutes with radiant energy according to the first radiant energy level and with pressure according to the first pressure level.

10. The method of claim 1 wherein the first pressure level is approximately 20,000 Pascal.

11. The method of claim 10 wherein the cannabis material is processed for 15 minutes with radiant energy according to the first radiant energy level and with pressure according to the first pressure level.

12. A method for processing cannabis, comprising:
    receiving cannabis material;
    performing an analysis of the cannabis material, wherein the type of analysis is selected from the group consisting of photographic/video analysis, laser analysis, spectral/spectrometer analysis, near infrared spectroscopy (NIR), moisture analysis, analysis of components, bioburden analysis, enzyme-linked immunoadsorbent assay (ELISA), gas chromatography (GC), high performance liquid chromatography (HPLC), thin layer chromatography (TLC), nuclear magnetic resonance (NMR), quantitative Polymerase Chain-Reaction (qPCR), and pesticide residue analysis;
    determining, based on the analysis, a radiant energy level;
    determining, based on the analysis, a pressure level;
    processing the cannabis material with radiant energy according to the radiant energy level and with pressure according to the pressure level,
    wherein the radiant energy level and the pressure level are determined to reduce the water activity of the cannabis material to below 0.60, and to maintain a terpene content of the cannabis material above a predetermined level.

13. The method of claim 12 wherein the radiant energy level is 7 kilowatts.

14. The method of claim 13 wherein the pressure level is approximately 40,000 Pascal.

15. The method of claim 14 wherein the cannabis material is processed for 10 minutes with radiant energy according to the radiant energy level and with pressure according to the pressure level.

16. The method of claim 12 wherein the pressure level is approximately 40,000 Pascal.

17. The method of claim 16 wherein the cannabis material is processed for 10 minutes with radiant energy according to the radiant energy level and with pressure according to the pressure level.

18. The method of claim 12 wherein the radiant energy level is 5 kilowatts.

19. The method of claim 18 wherein the pressure level is approximately 20,000 Pascal.

20. The method of claim 19 wherein the cannabis material is processed for 15 minutes with radiant energy according to the radiant energy level and with pressure according to the pressure level.

* * * * *